(12) United States Patent
Bonda et al.

(10) Patent No.: US 7,754,191 B2
(45) Date of Patent: *Jul. 13, 2010

(54) METHOD OF QUENCHING ELECTRONIC EXCITATION OF CHROMOPHORE-CONTAINING ORGANIC MOLECULES PHOTOACTIVE COMPOSITIONS

(75) Inventors: Craig A. Bonda, Winfield, IL (US); Anna Pavlovic, Elmwood Park, IL (US)

(73) Assignee: Hallstar Innovations Corp., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/290,732

(22) Filed: Nov. 3, 2008

(65) Prior Publication Data
US 2009/0057627 A1  Mar. 5, 2009

Related U.S. Application Data

(63) Continuation-in-part of application No. 11/891,280, filed on Aug. 9, 2007, and a continuation-in-part of application No. 12/022,758, filed on Jan. 30, 2008, now Pat. No. 7,588,702, which is a continuation-in-part of application No. 11/891,281, filed on Aug. 9, 2007, now Pat. No. 7,597,825.

(51) Int. Cl.
*A61K 8/18* (2006.01)
(52) U.S. Cl. .......................... 424/59; 424/60; 424/401; 252/301.35; 252/500; 252/589; 252/601; 514/520; 524/90; 558/410
(58) Field of Classification Search ................ 252/601, 252/301.35, 500, 336.1, 372, 461.1; 424/59, 424/60, 401; 428/412; 359/350, 361; 558/400; 560/81; 525/304
See application file for complete search history.

(56) References Cited

U.S. PATENT DOCUMENTS

| | | | |
|---|---|---|---|
| 2,623,060 A | 12/1952 | Cragoe | |
| 3,215,724 A | 11/1965 | Strobel et al. | |
| 3,337,357 A | 8/1967 | Strobel et al. | |
| 4,284,621 A | 8/1981 | Preuss et al. | |
| 4,293,542 A | 10/1981 | Lang et al. | |
| 4,307,240 A | 12/1981 | Ching | |
| 4,562,278 A | 12/1985 | Hill et al. | |
| 4,617,374 A | 10/1986 | Pruett et al. | |
| 4,707,537 A | 11/1987 | Pruett et al. | |
| 5,393,862 A * | 2/1995 | Jones et al. | 528/298 |
| 5,576,354 A | 11/1996 | Deflandre et al. | |
| 5,663,213 A | 9/1997 | Jones et al. | |
| 5,738,842 A | 4/1998 | Raspanti et al. | |
| 5,783,307 A * | 7/1998 | Fagerburg et al. | 428/412 |
| 5,989,528 A | 11/1999 | Tanner et al. | |
| 5,993,789 A | 11/1999 | Bonda et al. | |
| 6,001,952 A | 12/1999 | Carman et al. | |
| 6,113,931 A | 9/2000 | Bonda et al. | |
| 6,225,052 B1 | 5/2001 | Batz et al. | |
| 6,284,916 B1 | 9/2001 | Bonda et al. | |
| 6,485,713 B1 | 11/2002 | Bonda et al. | |
| 6,518,451 B2 | 2/2003 | Bonda et al. | |
| 6,537,529 B1 | 3/2003 | Bonda | |
| 6,551,605 B2 | 4/2003 | Bonda | |
| 6,800,274 B2 | 10/2004 | Bonda et al. | |
| 6,890,521 B2 | 5/2005 | Bonda | |
| 6,899,866 B2 | 5/2005 | Bonda | |
| 6,919,473 B2 | 7/2005 | Bonda et al. | |
| 6,962,692 B2 | 11/2005 | Bonda et al. | |
| 7,064,114 B2 | 6/2006 | Yiv et al. | |
| 7,201,893 B2 | 4/2007 | Wendel et al. | |
| 7,235,587 B2 | 6/2007 | Bonda et al. | |
| 7,292,156 B2 | 11/2007 | Smith et al. | |
| 7,449,698 B2 | 11/2008 | Nguyen et al. | |
| 7,534,420 B2 | 5/2009 | Bonda et al. | |
| 2002/0127192 A1 | 9/2002 | Murphy et al. | |
| 2003/0000130 A1 | 1/2003 | Wood et al. | |
| 2003/0176542 A1 | 9/2003 | Abe et al. | |
| 2004/0047817 A1 | 3/2004 | Bonda | |

(Continued)

FOREIGN PATENT DOCUMENTS

DE   1222926   8/1966

(Continued)

OTHER PUBLICATIONS

International Search Report for PCT/US2008/058456, dated Jun. 27, 2008.

(Continued)

*Primary Examiner*—Ling-Siu Choi
*Assistant Examiner*—Bijan Ahvazi
(74) *Attorney, Agent, or Firm*—Marshall, Gerstein & Borun LLP

(57) ABSTRACT

A method of quenching fluorescence of a naphthalate polyester that is subjected to UV-radiation in an amount sufficient to cause the naphthalate polyester to reach an excited state and fluoresce, comprising adding to the naphthalate polyester a fluorescence quenching amount of a compound of formula (1):

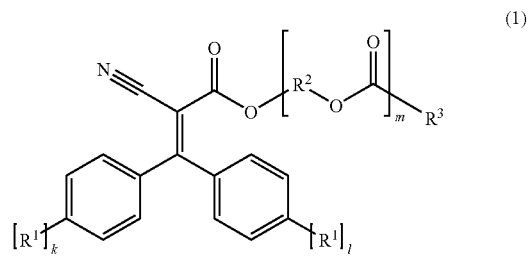

(1)

wherein $R^1$ is an alkoxy; $R^2$ is an organic linker; k is either zero or one; l is either zero or one, wherein the sum of k+l is one; and m is an integer in a range from zero to about twenty.

14 Claims, 4 Drawing Sheets

U.S. PATENT DOCUMENTS

| | | | |
|---|---|---|---|
| 2004/0166072 A1* | 8/2004 | Bonda | 424/59 |
| 2004/0170579 A1 | 9/2004 | Mobius | |
| 2005/0191249 A1 | 9/2005 | Bonda et al. | |
| 2006/0002869 A1* | 1/2006 | Bonda et al. | 424/59 |
| 2006/0228311 A1 | 10/2006 | Bonda et al. | |
| 2008/0286217 A1 | 11/2008 | Chaudhuri | |

FOREIGN PATENT DOCUMENTS

| | | |
|---|---|---|
| EP | 570838 | 11/1993 |
| EP | 0711803 A2 | 5/1996 |
| EP | 0761201 | 3/1997 |
| EP | 1323743 | 7/2003 |
| JP | 08225672 | 9/1996 |
| JP | 2005-139263 | 6/2005 |
| SU | 1273360 | 11/1986 |
| WO | WO-00/27337 | 5/2000 |
| WO | WO-0242368 | 5/2002 |
| WO | WO-2007/128840 | 11/2007 |

OTHER PUBLICATIONS

Written Opinion for PCT/US2008/058456, dated Jun. 27, 2008.
European Search Report for EP 08 10 3204, dated Jul. 17, 2008.
Horiba Jobin Yvon Ltd., A Guide to Recording Fluorescence Quantum Yields, www.jyhoriba.co.uk.
Cheung, P.-S. R., Roberts, C. W. "Photophysical Processes in Dimethyl 2,6-Naphthalenedicarboxylate and Poly(ethylene 2,6-Naphthalenedicarboxylate)" J. Polymer Sci.: Polymer Let. Ed., vol. 17, pp. 227-232 (1979).
Palm, M. D., O'Donoghue, M. N. "Update on Photoprotection" Dermatologic Therapy, vol. 20, pp. 360-376 (2007).
Senchenya, N. G., et al. "Silicon-containing esters of α-cyanoacrylic acid: synthesis and properties" Russian Chem. Bul., vol. 42(5), pp. 909-911 (1993).
"Light Absorbing Properties of Naphthalate Containing Polyesters" BP p.l.c., Technical Bulletin N-10, 1991.
"Amoco® NDC for Coatings, Inks and Adhesives" Amoco Chemicals, Bulletin FA-21b.
Baussard, "Chap. II: Donor-Acceptor pairs for Forster Resonance Energy Transfer (FRET):" in Synthesis of New Ionic Functional Polymers by Free Radical Polymerization via the RAFT Process, Dissertation, Catholic University of Louvain, Jan. 26, 2004.
Bonda, "Research Pathways to Photostable Sunscreens," *Cosmetics & Toiletries Magazine*, vol. 123, No. 2, pp. 1, 49-60, Feb. 5, 2008.
Chatelain et al., "Photostabilization of Butyl Methoxydibenzoylmethane (Avobenzone) and Ethylhexyl Methoxycinnamate by Bis-ethylhexyloxyphenol Methoxyphenyl Triazine (Tinosorb S), a New UV Broadband Filter", *Photochemistry and Photobiology*, 2003, vol. 74(3): pp. 401-406.
European Search Report for EP 08 10 3205, dated Jul. 25, 2008.
International Search Report and Written Opinion for PCT/US2008/058454, dated Sep. 23, 2008.
Katritzky et al., "Synthesis of 3,3-diarylphrrolidines from Diaryl Ketones", *ARKIVOC*, Gainesville, FL, United States, 2003, vol. 5, pp. 9-18, Arkat USA Inc. URL: http://arkatusa.org/zark/journal/2003/Bernath/GB-594J/594J.pdf.
Min et al., "Spectroscopic studies on the interaction of cinnamic acid and its hydroxyl derivatives with human serum albumin", *J. Mol. Structure*, 692:71-80 (2004).
Somsen et al., "Planar chromatography coupled with spectroscopic techniques", *J. Chromatography A*, 703:613-65 (1995).
Turro, et al., *Modern Molecular Photochemistry*, University Science Books (1991).

* cited by examiner

METHOD OF QUENCHING ELECTRONIC EXCITATION OF CHROMOPHORE-CONTAINING ORGANIC MOLECULES PHOTOACTIVE COMPOSITIONS

CROSS-REFERENCE TO RELATED APPLICATION

The present application is a continuation-in-part of co-pending application Ser. Nos. 11/891,280 filed Aug. 9, 2007 and 12/022,758 filed Jan. 30, 2008, which is a continuation-in-part of co-pending application Ser. No. 11/891,281 filed Aug. 9, 2007. The entire text of the priority applications are incorporated herein by reference in their entirety.

BACKGROUND OF THE INVENTION

1. Field of the Disclosure

The disclosure generally relates to photostabilized compositions containing an α-cyano-β,β-diphenylacrylate photostabilizer for a UV-absorbing naphthalate compound and, more specifically, to a naphthalate polymer composition containing an α-cyano-β,β diphenylacrylate photostabilizer. The disclosure further relates to polymer blends containing a naphthalate polymer and an α-cyano-β,β diphenylacrylate photostabilizer for the naphthalate polymer. The disclosure also is directed to methods of preparing and using photostabilized naphthalate or polyester-containing compositions.

2. Brief Description of Related Technology

Ultraviolet radiation from the sun or artificial sources can damage materials and/or coatings containing photoactive substances, such as photoactive polymers, pigments and dyes, by altering chemical bonds in the structure of the polymer, pigment, or dye. This photodegradation can lead to color fading, loss of gloss, and/or loss of physical and protective properties of a photodegradable or photoactive polymer or coating. Understandably, photostabilizing or photostabilization is the process or effect of preventing the photodegradation of photoactive substances. In particular, photostabilizing can be increasing the light fastness of a composition, preventing yellowing, or color formation, and delaying or preventing photochemical reactions that adversely affect photoactive substances.

One method to protect photoactive substances is through the use of UV filters; one class of materials particularly suited to act as a UV filters are naphthalate polyesters, for example those patented by this assignee. Naphthalate polyesters are suitable UV filters because they have very high extinction coefficients and subsequently low transmission of ultraviolet (UV) radiation. Additionally, the incorporation of naphthalates into polyester polymers increase the polymer's thermal and structural stability, decrease the polymer's gas permeability, and dramatically block the transmission of UV radiation through the polymer. The UV filtering and improved physical characteristics have led to the use of naphthalate polymers and blends in a wide range of applications including beverage and personal care product packaging, protective screening films, sail cloth fiber and as an additive stabilizer in sunscreens and cosmetics.

While efficiently absorbing UV radiation, naphthalates dissipate (emit) the absorbed energy through fluorescence. Fluorescence is a type of luminescence in which an atom or molecule emits radiation, i.e., a photon, in passing from a higher to a lower electron state, as described in my co-pending application Ser. No. 11/891,280 filed Aug. 9, 2007, herein incorporated by reference. The term is restricted to phenomena in which the time interval between absorption and emission energy is extremely short ($10^{-12}$ to $10^{-6}$ second). This fluorescence can be a positive attribute in enabling the ready detection of naphthalate containing polymers or in the development of fluorescent coatings and inks. Alternatively, the high absorption of UV radiation can produce color formation or yellowing after exposure to UV light. Although this yellowing may not impact mechanical and physical properties of the polymer, it is generally undesirable. The fluorescence, color formation, or yellowing phenomena are of concern especially in packaging of products when the product's appearance is to be as close to its natural state as desired. For example, in the packaging of foods and beverages, if food or beverages were inside a poly(ethylene-2,6-naphthalene dicarboxylate) ("PEN") container they may appear unnaturally colored.

Quenching fluorescence eliminates or reduces photon emission by providing an alternative pathway for the excited state energy, such as radiative loss (heat), or intersystem crossing to an excited triplet state. Methods to quench fluorescence in PEN have been disclosed, for example see references cited in U.S. Pat. No. 6,001,952. These examples disclose the use of o-chlorophenol to quench PEN fluorescence in chloroform solutions. Dissolving PEN in a chloroform solution to disperse a fluorescence quencher, however, is not practical since the PEN must have a low molecular weight to dissolve in the chloroform solution and only very dilute PEN solutions can be prepared.

Other compounds used to quench naphthalate fluorescence include: benzotriazoles, cyanoacrylates, benzophenones, and benzoxazinones (JP Pat. No. 08225672); cyclic imino esters or quinoxalines (EP Pat. No. 0711803); and benzylidene compounds (U.S. Pat. Nos. 4,617,374, 4,707,537, and 6,001, 952). Many of these examples are disadvantageous because they require post production coating of fluorescent materials, show inadequate reduction in the fluorescence from fluorescent materials, or are only effective in very dilute solutions. Accordingly, there is a need for naphthalate compositions having a reduced fluorescence without deleteriously affecting the physical properties of the polymer.

Generally, the prior art does not teach or suggest to one of ordinary skill in the art how to quench the fluorescence of naphthalate compounds and compositions with α-cyano-β,β-diphenylacrylates.

SUMMARY OF THE INVENTION

Disclosed herein are compositions of naphthalate polyesters and photostabilizing α-cyano-β,β-diphenylacrylates that reduce (quench) the fluorescence of the naphthalate polyesters, enhance the photostability of the naphthalate polyesters, and improve the photoprotection provided by a composition containing the photostabilized naphthalate polyesters.

One aspect of the compositions and methods described herein is to provide a naphthalate polyesters containing composition and a photostabilizer thereof.

Another aspect of the compositions and methods described herein is to provide a polymer composition containing a naphthalate polyester and a photostabilizing chromophore thereof.

Yet, another aspect of the compositions and methods described herein is to provide a sunscreening composition containing a naphthalate polyesters compounds and a photostabilizing α-cyano-β,β-diphenylacrylate.

An additional aspect of the compositions and methods described herein is to provide a photostabilized naphthalate polyester capable of protecting objects from exposure to UV radiation.

Additional features of the invention may become apparent to those skilled in the art from a review of the following detailed description, taken in conjunction with the drawings, the examples, and the appended claims.

BRIEF DESCRIPTION OF THE DRAWING FIGURES

For a more complete understanding of the disclosure, reference should be made to the following detailed descriptions and accompanying drawings wherein:

FIG. 1 is a color photograph of a thin layer chromatography plate showing the effect of ethylhexyl methoxycrylene having a formula:

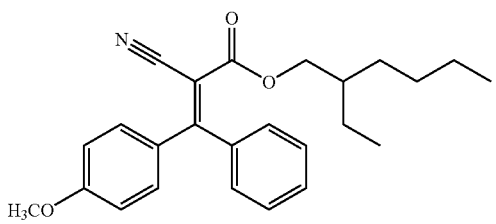

on naphthalate polyester fluorescence, specifically on diethylhexyl-2,6-naphthalate fluorescence. The photograph shows two rows of three spots; the lower row 200, a reference row, shows the unquenched fluorescence of diethylhexyl-2,6-naphthalate and the upper row 110 shows the effect of zero weight percent 111, 25 weight percent 112, and 50 weight percent 113 of ethylhexyl methoxycrylene on the fluorescence of diethylhexyl-2,6-naphthalate. The photograph shows the complete quenching by the darkening of the spot of naphthalate polyester fluorescence at 25 mole percent diethylhexyl-2,6-naphthalate 112.

Figure 1:
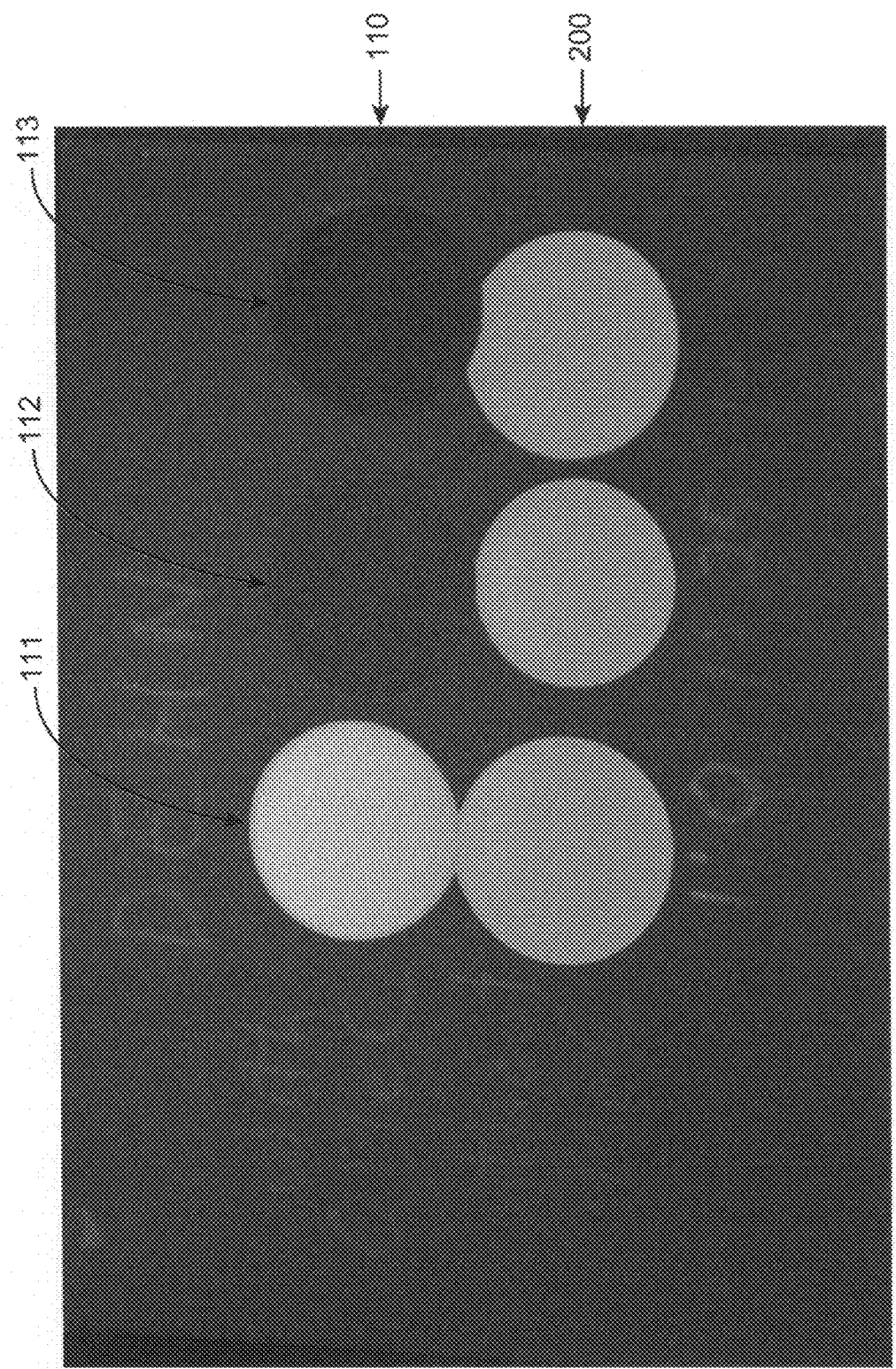
FIG. 1 is a photograph of a thin layer chromatography plate showing the effect of ethylhexyl methoxycrylene.
Figure 2:
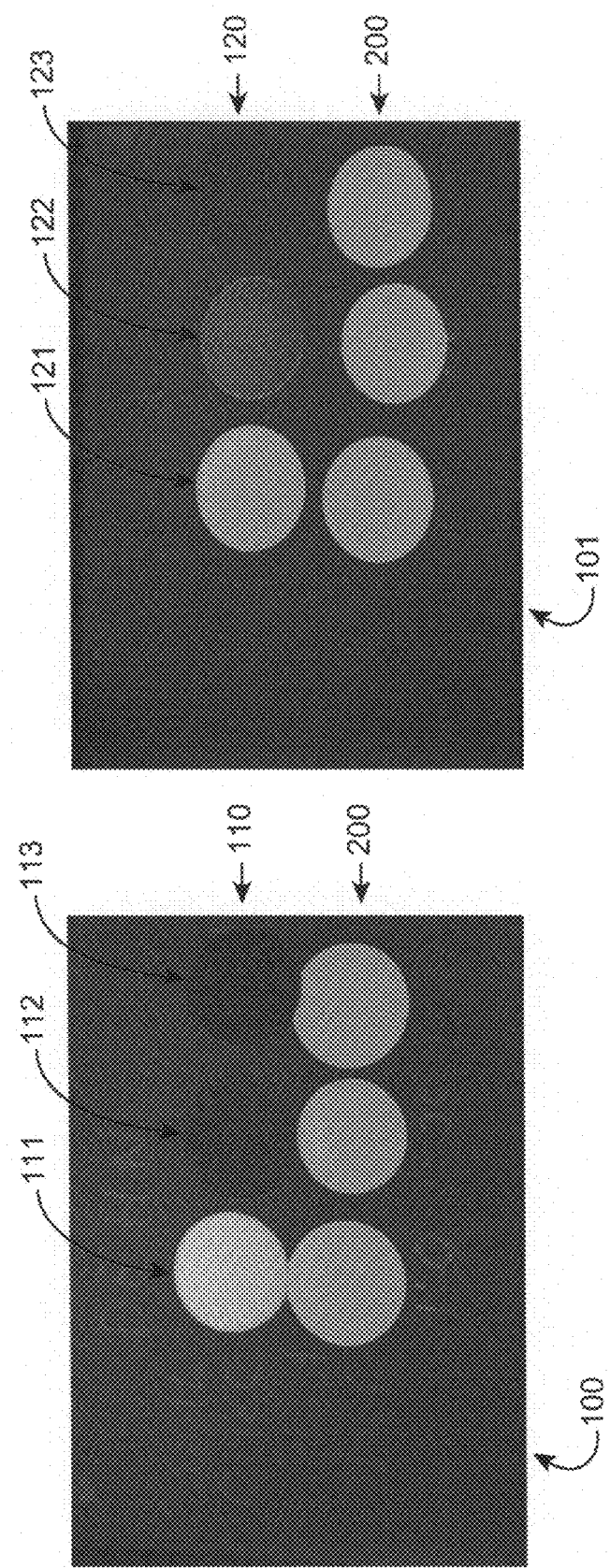
FIG. 2 is a comparison of two photographs of thin layer chromatography plates showing the effects of ethylhexyl methoxycrylene and of octocrylene on diethylhexyl-2,6-naphthalate fluorescence.

FIG. 2 is a comparison of two color photographs of thin layer chromatography plates showing the effects of ethylhexyl methoxycrylene and of octocrylene on diethylhexyl-2,6-naphthalate fluorescence. The left photograph 100 shows the effect of ethylhexyl methoxycrylene on diethylhexyl-2,6-naphthalate fluorescence with two rows of three spots; the lower row 200, a reference row, shows the unquenched fluorescence of diethylhexyl-2,6-naphthalate and the upper row 110 shows the effect of zero weight percent 111, 25 weight percent 112, and 50 weight percent 113 of ethylhexyl methoxycrylene on the fluorescence of diethylhexyl-2,6-naphthalate. The right photograph 101 shows the effect of octocrylene on diethylhexyl-2,6-naphthalate fluorescence with two rows of three spots; the lower row 200, a reference row, shows the unquenched fluorescence of diethylhexyl-2,6-naphthalate and the upper row 120 shows the effect of zero mole percent 121, 25 mole percent 122, and 50 mole percent 123 of octocrylene on the fluorescence of diethylhexyl-2,6-naphthalate. Comparison of the two photographs shows that the spot corresponding to 50 mole percent of octocrylene 123 is lighter than the spot corresponding to 25 mole percent ethylhexyl methoxycrylene 112, indicating less effective quenching of diethylhexyl-2,6-naphthalate fluorescence by the octocrylene.

Figure 3:
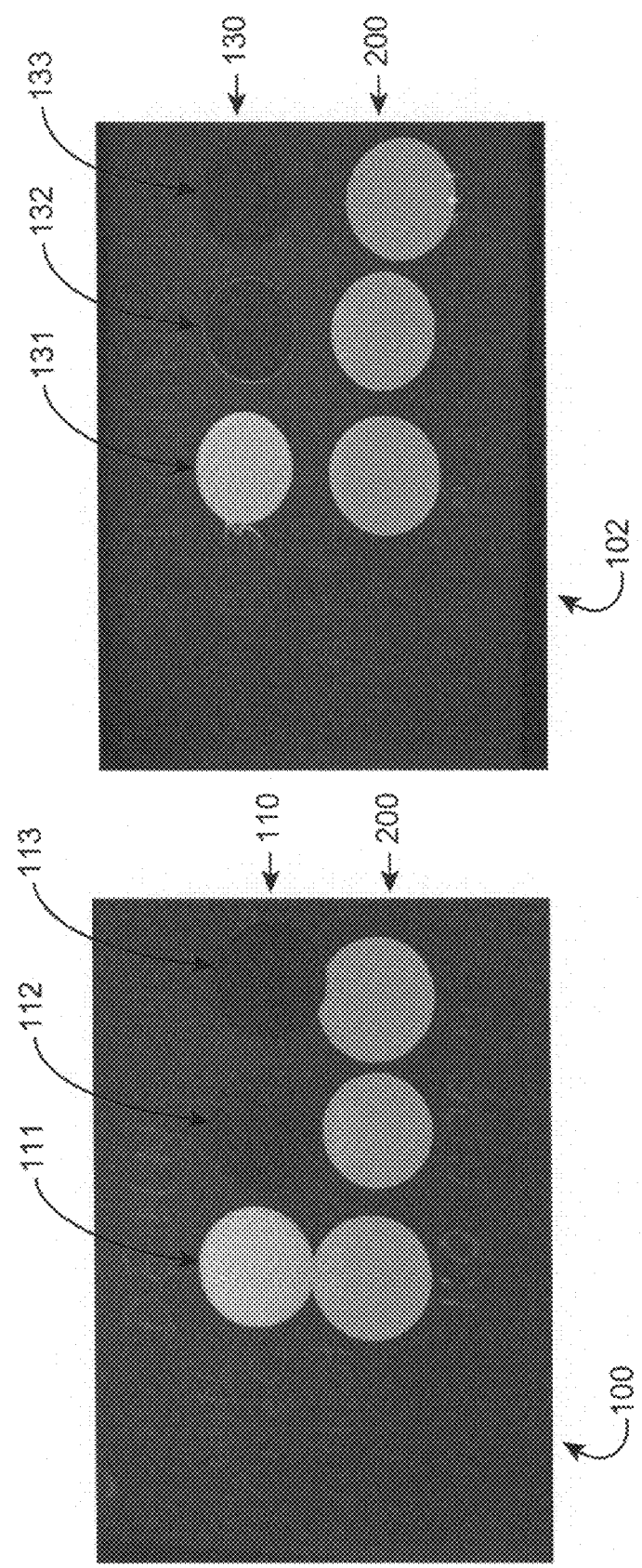
FIG. 3 is a comparison of two photographs of thin layer chromatography plates showing the effects of ethylhexyl methoxycrylene and of benzophenone-3 on diethylhexyl-2,6-naphthalate fluorescence.

FIG. 3 is a comparison of two color photographs of thin layer chromatography plates showing the effects of ethylhexyl methoxycrylene and of benzophenone-3 on diethylhexyl-2,6-naphthalate fluorescence. The left photograph 100 shows the effect of ethylhexyl methoxycrylene on diethylhexyl-2,6-naphthalate fluorescence with two rows of three spots; the lower row 200, a reference row, shows the unquenched fluorescence of diethylhexyl-2,6-naphthalate and the upper row 110 shows the effect of zero weight percent 111, 25 weight percent 112, and 50 weight percent 113 of ethylhexyl methoxycrylene on the fluorescence of diethylhexyl-2,6-naphthalate. The right photograph 102 shows the effect of benzophenone-3 on diethylhexyl-2,6-naphthalate fluorescence with two rows of three spots; the lower row 200, a reference row, shows the unquenched fluorescence of diethylhexyl-2,6-naphthalate and the upper row 130 shows the effect of zero mole percent 131, 25 mole percent 132, and 50 mole percent 133 of benzophenone-3 on the fluorescence of diethylhexyl-2,6-naphthalate. Comparison of the two photographs shows that the spot corresponding to 50 mole percent of benzophenone-3 133 is approximately the same shade as the spot corresponding to 25 mole percent ethylhexyl methoxycrylene 112, indicating less effective quenching of diethylhexyl-2,6-naphthalate fluorescence by the benzophenone-3.

Figure 4:
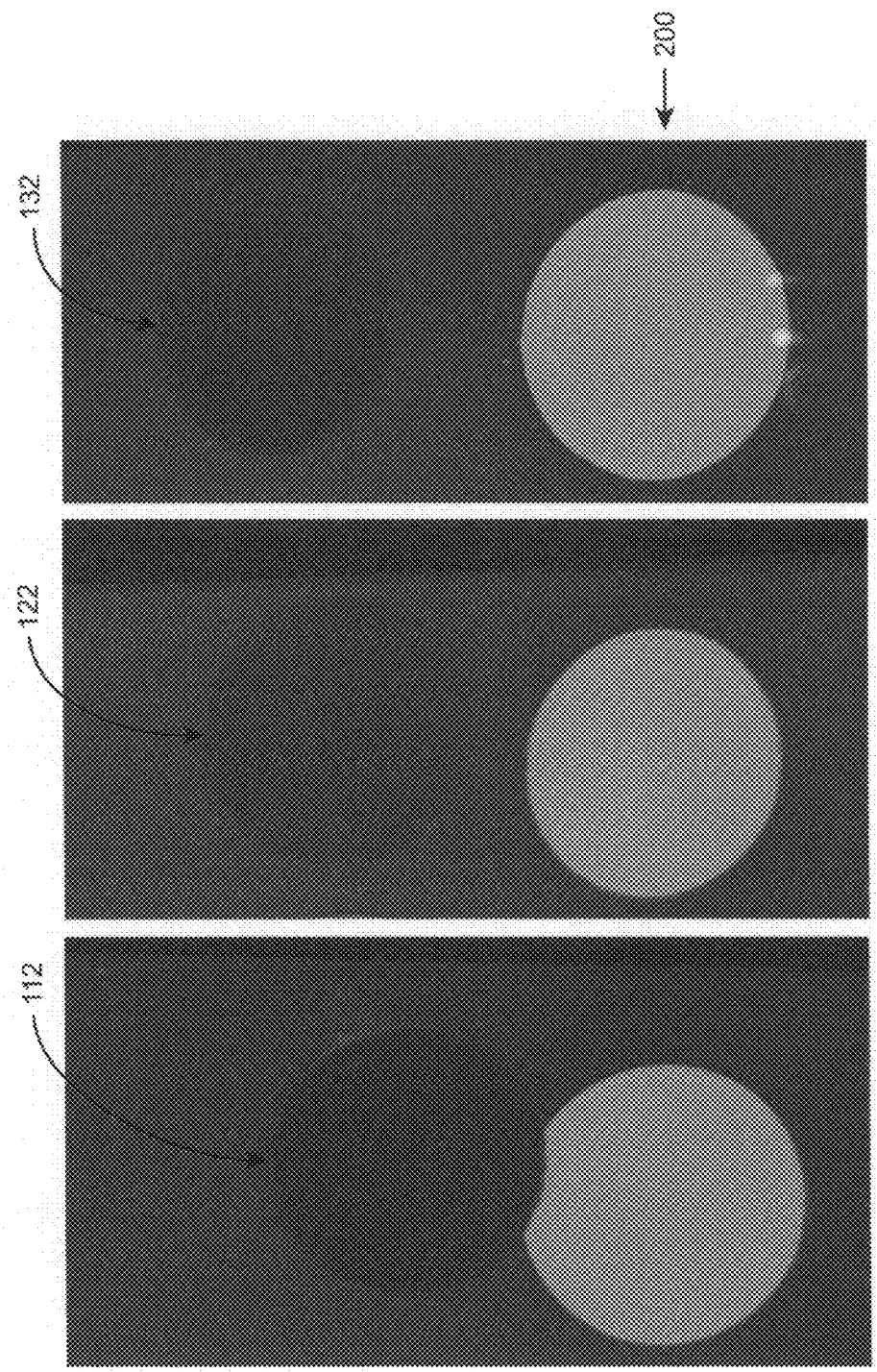
FIG. 4 is a comparison of color photographs of thin layer chromatography plates showing the effects of ethylhexyl methoxycrylene 112, octocrylene 122, and benzophenone-3 132 on diethylhexyl-2,6-naphthalate fluorescence.

FIG. 4 is a comparison of three color photographs of thin layer chromatography plates showing the effects of ethylhexyl methoxycrylene 112, octocrylene 122, and benzophenone-3 132 on diethylhexyl-2,6-naphthalate fluorescence. The photographs provide a comparison of diethylhexyl-2,6-naphthalate fluorescence 200 and the fluorescence from a mixture of diethylhexyl-2,6-naphthalate and ethylhexyl methoxycrylene 112, octocrylene 122, and benzophenone-3 132. The photographs clearly show the effective quenching of diethylhexyl-2,6-naphthalate fluorescence by ethylhexyl methoxycrylene 112 and incomplete quenching by octocrylene 122, and benzophenone-3 132.

The patent or application file contains at least one drawing executed in color. Copies of this patent or patent application with color drawing(s) will be provided by the Office upon request and payment of the necessary fee.

While the disclosed compositions and methods are susceptible of embodiments in various forms, there are illustrated in the photographs (and will hereafter be described) specific embodiments of the invention, with the understanding that the disclosure is intended to be illustrative, and is not intended to limit the invention to the specific embodiments described and illustrated herein.

DETAILED DESCRIPTION OF THE INVENTION

Herein, ranges may be expressed as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "alkoxy" herein refers to a radical having the formula O-(alkyl), wherein (alkyl) is an alkyl radical, straight chain or branched, having 1 to 30 carbon atoms, preferably with one to eight carbon atoms, more preferably with one carbon atom (e.g., where alkoxy is methoxy).

The invention generally relates to UV absorbing compositions having a naphthalate polyester together with an alkoxycrylene photostabilizer. Compositions including the naphthalate and the photostabilizer have enhanced photostability and prolonged photoprotection. Additionally, compositions described herein exhibit, unexpectedly, decreased fluorescence upon exposure to UV radiation.

The compositions described herein can be prepared by combining a naphthalate polyester with an alkoxycrylene photostabilizer. The naphthalate polyesters are naphthalene-dicarboxalates and have either of the following general formula (I) or (II):

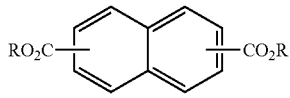
(I)

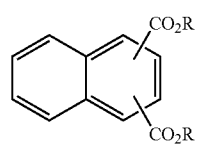
(II)

where R is an organic group, defined hereinafter. Specifically, each discrete naphthalate polyester has two R groups that can be the same or different. Dialkylnaphthalates are those naphthalate polyesters where the R groups are alkyl groups, the alkyl groups can be linear, branched, or cyclic and have 1 to about 20 carbon atoms. Non-limiting examples of dialkylnaphthalates include those compounds with the following specific structures:

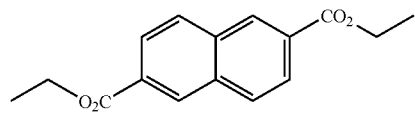

-continued

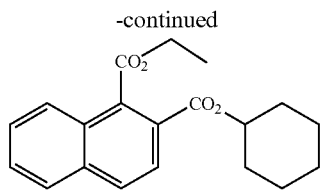

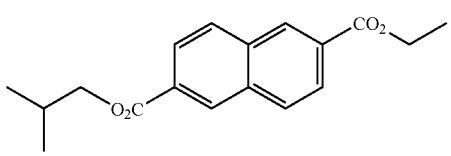

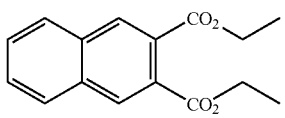

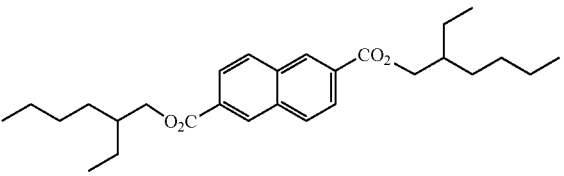

Naphthalate oligomers are those naphthalate polyester compounds where a fraction of the R groups bridge between naphthalene groups. Naphthalate oligomers are distinguishable from naphthalate polymers by the number of naphthalene groups, in particular naphthalate oligomers have 2 to about 50 naphthalene groups. Naphthalate oligomers have R groups that can be the same or different, the R groups on a fraction of the naphthalate oligomers bridge to other naphthalene groups while two R groups per naphthalate oligomer do not bridge to another naphthalene group. Naphthalate oligomers can consist of naphthalate polyesters having entirely general formula (I), entirely general formula (II), or a mixture of general formula (I) and general formula (II), as defined above. By way of non-limiting example, naphthalate oligomers can have the following specific and/or general structures, where n is an integer from 0 to about 50:

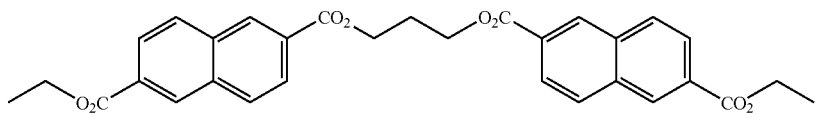

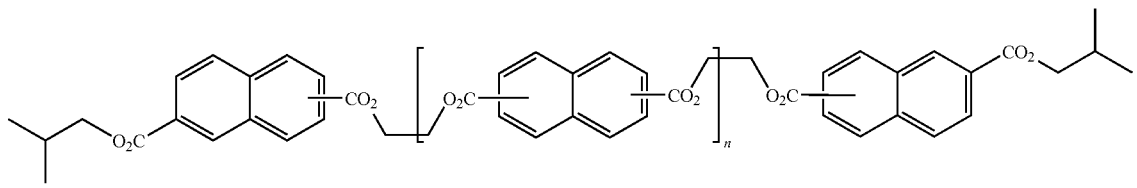

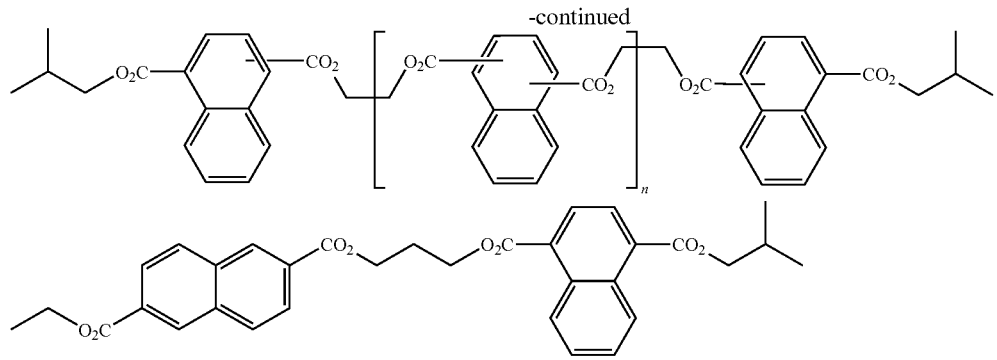

Naphthalate polymers are those naphthalate polyester compounds where the R groups bridge between naphthalene groups. Naphthalate polymers are distinguishable from naphthalate oligomers by the number of naphthalene groups, in particular naphthalate polymers have more than about 50 naphthalene groups. In naphthalate polymers the bridging R groups can be the same or different. Naphthalate polymers can consist of naphthalate polyesters having entirely general formula (I), entirely general formula (II), or a mixture of general formula (I) and general formula (II), as defined above. One commercially available naphthalate polymer is polyethylene 2,6-naphthalate ("PEN"; poly(ethylene 2,6-naphthalenedicarboxylate)). Additional naphthalate polymers include those disclosed in U.S. Pat. No. 6,001,952 and the text thereof is included herein for those polymers. By way of non-limiting example, naphthalate polymers can have either of the general formula:

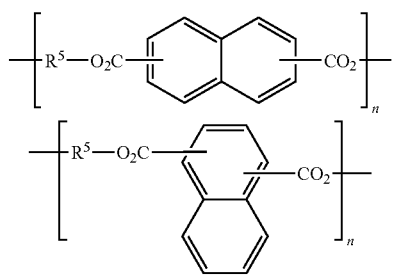

wherein $R^5$ is a straight or branched $C_1$-$C_{10}$ alkyl chain, and n is an integer, or consist of a copolymer of the two pictured formula. Additionally, this copolymer can be a random copolymer or a block copolymer.

Likewise, naphthalate polyesters can additionally be naphthalate copolymers. As used herein naphthalate copolymers, and differentiated from naphthalate polymers that can be block or random copolymers of naphthalate polyesters (described above), are block type polymers with a naphthalate polymer block and an alternative polymer block. The alternative polymer block can be, for example polyesters, e.g., polyethelene terphthalate; polyalkenes, e.g., polyethylene, polypropylene, polystyrene; polyglycols, e.g., polyethylene glycol; polyimines, and polyacrylates. One of ordinary skill in the art understands that the difference between polymers and oligomers is simply one of degree, that is the number of discrete units in the representative chain, correspondingly the above discloser for the naphthalate polymers and copolymers applies to naphthalate oligomers as oligomers can be block type or random type oligomers.

The photostabilizing chromophores described herein are alkoxycrylene compounds of the formula (1):

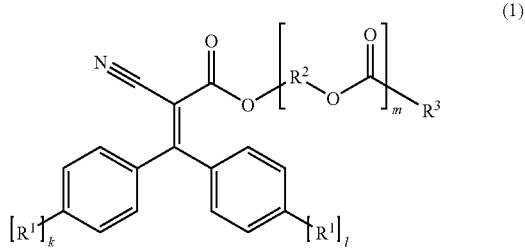

wherein $R^1$ is an alkoxy, preferably methoxy or ethoxy; $R^2$ is an organic linker; $R^3$ is a straight or branched $C_1$-$C_{30}$ alkyl, a straight or branched $C_1$-$C_{30}$ alkenyl, a straight or branched $C_1$-$C_{30}$ alkynyl, or a polymer chain (a "$R^3$-polymer chain"), k is either zero or one; l is either zero or one, wherein the sum of k+l is one; and m is an integer in a range from zero to about twenty. A $R^3$-polymer chain is an polyolefinic, polyacetylinic, polyesteric, or polyglycolic chain or fragment thereof; for example, a polyethylene chain, a polypropylene chain, a polyacetylene chain, a polyethylene terephthalate chain, or a polyethylene glycol chain. By way of non-limiting examples, the photostabilizing chromophore can have the following specific structures:

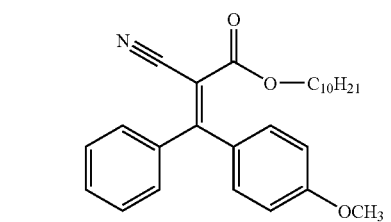

m = 0
k = 0
l = 1

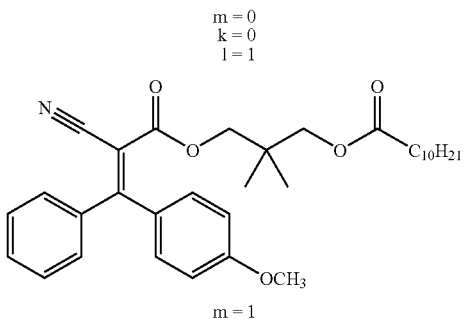

m = 1

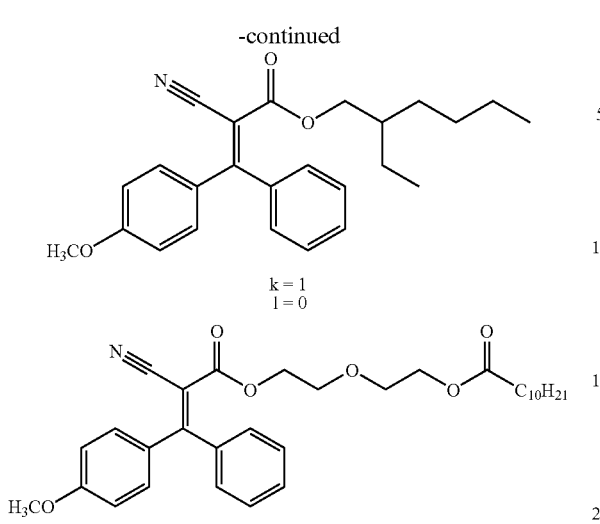

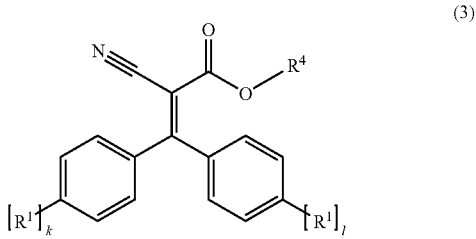

ticular, branched alkyl chains are preferred and one preferred branched alkyl chain is 2,2-dimethylpropyl ($CH_2C(CH_3)_2CH_2$).

Additionally, the photostabilizing chromophores described herein are alkoxycrylene compounds of the formula (3):

wherein k is either zero or one; l is either zero or one, the sum of k+l is one, $R^1$ is selected from a group consisting of methoxy and ethoxy; and $R^4$ is a naphthalate polyester comprising a formula (4):

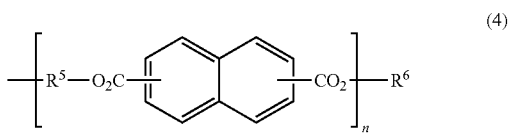

Suitable organic linkers ($R^2$) can be, for example, linear, cyclic, and/or branched alkyl chains; alkyl chains containing aromatic groups; aromatic groups; glycolates; dialkylthioethers; dialkylamines; or mixtures thereof. Preferred organic linkers are linear alkyl chains, branched alkyl chains, and glycolates. In particular, organic linkers can be groups having 1 to 20 carbon atoms and assembled individually or from a mixture of the following fragments of $CH_2$, $CH_2CH_2$, $CH_2CH_2CH_2$, $CH_2CH(CH_3)CH_2$, $CH_2C(CH_3)_2CH_2$, $CH_2OCH_2$, $CH_2CH_2OCH_2CH_2$. Non-limiting examples include ethyl ($CH_2CH_2$), ethylene glycolate ($CH_2CH_2OCH_2CH_2$), 2-methylpropyl ($CH_2CH(CH_2)CH_2$), and ethylpropylglycolate ($CH_2CH_2OCH_2CH_2CH_2$). In parwhere $R^5$ is a straight or branched $C_1$-$C_{10}$ alkyl chain; $R^6$ is a hydrogen atom, a straight or branched $C_1$-$C_{20}$ alkyl chain, or a photostabilizing chromophore; and n is an integer ranging from one to about 2000. By way of non-limiting examples, the photostabilizing chromophore can have the following specific structures:

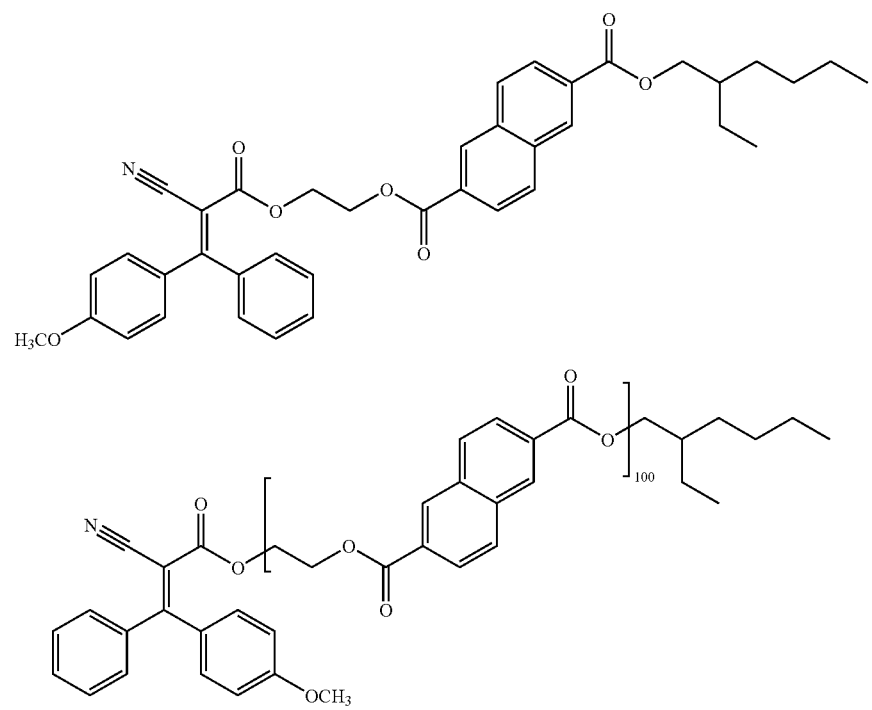

The composition described herein can additionally contain polymer additives, for example, other polymers, plastics, plasticizers, elastomers, slip additives, antistatic additives, antiblocking additives, electroconductive additives, flame retardants, antioxidants, curatives, lubricants, dyes, inks, and/or powders. Representative examples of additives include polyethylene terephthalate ("PET"), polycarbonate, acrylic urethane, carbon fiber, 2-hydroxyethylamine, polyethylene terphthalate copolymer; polyimide; polyimide copolymer; polyethylene; polyethylene copolymer; polystyrene; polystyrene copolymer; polypropylene; polypropylene copolymer; mixtures and/or blends thereof.

Useful polyesters include PET, PET copolyester containing up to 20 mole % isophthalic acid, PET copolyester containing up to 70 mole % 1,4-cyclohexanedimethanol, PET copolyester containing up to 37 mole % diethylene glycol, PET copolyester containing up to 50 mole % 1,4-butanediol, poly(1,4-butyleneterephthalate) (PBT), PBT copolyester containing up to 15 mole % ethylene glycol, poly(ethylene-1,4-cyclohexanedicarboxylate), poly(1,4-cyclohexyldimethylene terephthalate) ("PCT"), PCT copolyester containing up to 18 mole % ethylene glycol, PCT copolyester containing up to 40 mole percent isophthalic acid, polycarbonate and the like. All of these polyesters are readily prepared by methods well known to those skilled in the art.

Blends of the composition with polymer additives generally contain about 0.1 weight percent to about 99.9 weight percent of the naphthalate-photostabilizing chromophore composition. Such blends can be readily prepared using conventional melt processing equipment such as a Brabender extruder, single-screw extruder, twin-screw extruder and the like. The blends are generally processed at temperatures in the range of about 260° C. to about 330° C. The methods of blending and formulating compositions for specific applications will be available to those of ordinary skill in the art.

Specific applications for the disclosed compositions include food packaging such as bottles, trays, lids and films, medical parts, appliance parts, automotive parts, tool housings, recreational and utility parts. The compositions of the present invention are especially useful in applications that require transparent molded parts. Additionally, the polymers can be used to prepare extruded sheets for thermoforming applications. The compositions are readily extruded into films or processed into monolayer or multi layer food and beverage containers. Potential methods for producing containers include: (1) injection stretch blow molding using either one or two stage technology, (2) injection blow molding, (3) extrusion blow molding, (4) pipe extrusion, and (5) co-injection or co-extrusion where the polymers can serve as either the structural layer or barrier layer depending upon end use requirements. Fibers, melt-blown webs, extruded sheets, vacuum-drawn trays/parts, injection molded parts, and extrusion coated wires may also be made from these compositions. Many other ingredients can be added to enhance the performance properties of the disclosed compositions. For example, surface lubricants, denesting agents, stabilizers, antioxidants, mold release agents, metal activators, colorants such as black iron oxide and carbon black, nucleating agents, phosphate stabilizers, zeolites, fillers and the like can be included. All of these additives and the use thereof will be apparent to those of ordinary skill in the art.

Additionally, the composition described herein can function as a sunscreening composition, these compositions generally include UV-A and UV-B photoactive compounds in a cosmetically acceptable carrier, optionally including additives, such as emollients, stabilizers, emulsifiers, and combinations thereof. Additives can include cosmetically acceptable emollients, stabilizers, emulsifiers, thickeners, humectants, surfactants, preservatives, vitamins, antifoaming agents, fragrances, anti-irritants, organomodified silicones, chelators, opacifiers, polar oils, nonpolar oils, waxes, alcohols, polyols, propellants, colorants, and pigments. A typical sunscreening composition includes one or more photoactive compounds, wherein the photoactive compound(s) act to absorb UV radiation and thereby protect the substrate (e.g., human skin, resins, films, and the like) from the harmful effects of UV radiation. The absorption process causes a photoactive compound to reach an excited state, wherein the excited state is characterized by the presence of excited electronic energy (e.g., singlet state energy or triplet state energy), as compared to the ground state of the photoactive compound. Once a photoactive compound reaches an excited state there exists a number of pathways by which the excited photoactive compound can dissipate its excess energy (e.g., singlet and/or triplet energy), however, many of those pathways adversely affect the ability of the photoactive compound to further absorb UV radiation. The photostabilizing chromophores described herein accept electronic excited state energy from UV-absorbers, particularly naphthalate compounds, Avobenzone, octyl methoxycinnamate (Octinoxate), and octyl salicylate (Octisalate). The photostabilizing chromophores also are very effective UV-A absorbers in addition to providing excited state quenching of other UV-absorbing compounds in sunscreen compositions. The photostabilizing chromophores molecules described herein are especially effective when combined with one or more additional excited state quenching compounds such as oxybenzone.

The compositions disclosed herein can include a variety of photoactive compounds, preferably including one or more UV-A photoactive compounds and/or one or more UV-B photoactive compounds. Preferably, a sunscreen composition includes one or more photoactive compound selected from p-aminobenzoic acid and salts and derivatives thereof; anthranilate and derivatives thereof; dibenzoylmethane and derivatives thereof; salicylate and derivatives thereof; cinnamic acid and derivatives thereof (e.g., 2-ethylhexyl methoxycinnamate); dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives; methoxy-substituted benzophenone derivatives; uric acid derivatives; vilouric acid derivatives; tannic acid and derivatives thereof; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof. More preferably, a sunscreen composition includes a naphthalate polyester, a photostabilizing chromophore, a cinnamic acid derivative, and a dibenzoylmethane derivative. Still more preferably, a sunscreen composition includes a naphthalate polyester, a photostabilizing chromophore, 2-ethylhexyl methoxycinnamate, and 4-tert-butyl-4-methoxy dibenzoylmethane.

UV-A radiation (about 320 nm to about 400 nm), is recognized as contributing to causing damage to skin, particularly to very lightly colored or sensitive skin. A sunscreen composition disclosed herein preferably includes a UV-A photoactive compound. Preferably, a sunscreen composition disclosed herein includes a dibenzoylmethane derivative UV-A photoactive compound. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane; and combinations thereof.

For a product marketed in the United States, preferred cosmetically acceptable photoactive compounds and concentrations (reported as a percentage by weight of the total cosmetic sunscreen composition) include: aminobenzoic acid (also called para-aminobenzoic acid and PABA; 15% or less), Avobenzone (also called butyl-methoxy-dibenzoylmethane; 3% or less), cinoxate (also called 2-ethoxyethyl-p-methoxycinnamate; 3% or less), dioxybenzone (also called benzophenone 8; 3% or less), homosalate (also called 3,3,5-trimethylcyclohexyl salicylate, 15% or less), menthyl-anthranilate (also called menthyl-2-aminobenzoate; 5% or less), octocrylene (also called 2-ethylhexyl-2-cyano-3,3-diphenylacrylate; 10% or less), octyl-methoxycinnamate (7.5% or less), octyl salicylate (also called 2-ethylhexyl-salicylate; 5% or less), oxybenzone (also called benzophenone-3; 6% or less), padimate O (also called octyl-dimethyl PABA; 8% or less), phenylbenzimidazole sulfonic acid (water soluble; 4% or less), sulisobenzone (also called benzophenone-4; 10% or less), titanium dioxide (25% or less), trolamine salicylate (also called triethanolamine salicylate; 12% or less), and zinc oxide (25% or less).

Other preferred cosmetically acceptable photoactive compounds and preferred concentrations (percent by weight of the total cosmetic sunscreen composition) include diethanolamine-methoxycinnamate (10% or less), ethyl-[bis(hydroxypropyl)]-aminobenzoate (5% or less), glyceryl-aminobenzoate (3% or less), 4-isopropyl-dibenzoylmethane (5% or less), 4-methylbenzylidene camphor (6% or less), terephthalylidene-dicamphor sulfonic acid (10% or less), and sulisobenzone (also called benzophenone-4, 10% or less).

For a product marketed in the European Union, preferred cosmetically acceptable photoactive compounds and preferred concentrations (reported as a percentage by weight of the total cosmetic sunscreen composition) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene-dicamphor sulfonic acid (10% or less, expressed as acid), butyl-methoxydibenzoylmethane (5% or less), benzylidene-camphor sulfonic acid (6% or less, expressed as acid), octocrylene (10% or less, expressed as acid), polyacrylamidomethyl-benzylidene camphor (6% or less), ethylhexyl-methoxycinnamate (10% or less), PEG 25 PABA (10% or less), isoamyl-p-methoxycinnamate (10% or less), ethylhexyl-triazone (5% or less), drometrizole-trielloxane (15% or less), diethylhexyl-butamidotriazone (10% or less), 4-methylbenzylidene-camphor (4% or less), 3-benzylidene-camphor (2% or less), ethylhexyl-salicylate (5% or less), ethylhexyl-dimethyl PABA (8% or less), benzophenone-4 (5%, expressed as acid), methylene-bis-benztriazolyl-tetramethylbutylphenol (10% or less), disodium phenyl-dibenzimidazole tetrasulfonate (10% or less, expressed as acid), bisethylhexyloxyphenol methoxyphenol triazine (10% or less), methylene-bisbenzotriazolyl tetramethylbutylphenol (10% or less, also called TINOSORB M or Bisoctrizole), and bisethylhexyloxyphenol methoxyphenyl triazine (10% or less, also called TINOSORB S or Bemotrizinol).

In addition to observing an unexpected decrease in the fluorescence from naphthalate compounds and an increase in the photostability of naphthalate compositions, the disclosed composition effectively protects objects from UV radiation. When the disclosed composition is formulated and used as, for example, a plastic sheet or window, incident UV radiation is effectively filtered out. Applications for UV filtering plastic sheets or windows include residential, commercial, and vehicular windows, eye treatments (e.g., sunglasses and eyeglasses), picture framing, document protection, and any analogous application where UV radiation may have a deleterious effect on an object. Effective filtering of UV radiation by the disclosed compositions in such cases involves positioning or orienting the disclosed composition between the object to be protected from UV radiation and the UV radiation source. Additional usage includes applying the disclosed composition directly to the surface of the object to be protected, a non-limiting illustrative example is laminating. Additionally, usage includes wrapping the object to be protected in the disclosed composition, a non-limiting illustrative example is wrapping food with a plastic wrap of the disclosed composition. Combined within applying the disclosed composition to the surface of a object to be protected and wrapping the object in the disclosed composition are containers comprising the disclosed composition that hold objects to be protected, a non-limiting illustrative example is beer bottles wherein the beer is the object to be protected from UV radiation. Still another usage includes surrounding the UV source with the disclosed composition, non-limiting illustrative examples are covers, cases, or sleeves, e.g., for containing light bulbs and the structural components of light bulbs.

An additional method for using the disclosed composition is to blend or mix the disclosed composition with the object to be protected. Often the object to be protected is a photodegradable composition, for example inks, dyes, paints, and colorants.

Still another method for using the disclosed composition is to apply the disclosed composition directly to the surface of an object to be protected. The disclosed composition can be applied to the surface of the object in the form of sunscreens, lotions, sprays, paints, wipes, coatings, powders, and other forms that will be known to those of ordinary skill in the art.

One general method for preparing photoprotective chromophores can be understood from the specific procedures outlined below. In a large flask are combined 4-ethoxy benzophenone and ethyl cyanoacetate in a ratio of 1:1.35. The materials are then dissolved in a 5:1 mixture of toluene and acetic acid; followed by the addition of 0.1 mole equivalence of an ammonium acetate catalyst. The mixture is heated and any water formed during the reaction is distilled from the reaction mixture. Then the reaction mixture is cooled to room temperature and ethyl acetate is added to dissolve the solids and the mixture is washed with water. Then solvents are removed by distillation. The final solid product is re-crystallized from either hot methanol or a toluene/methanol mixture. The overall reaction is summarized as follows:

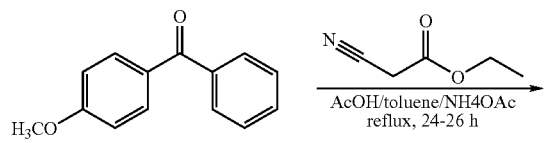

-continued

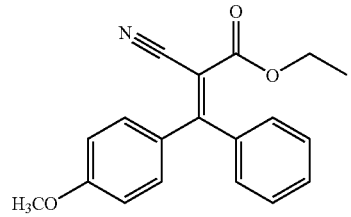

The ethyl α-cyano-β,β-diphenylacrylate can then be converted into a photostabilizing chromophore of formula (1) by treating it with 2-ethylhexanol in the presence of a catalyst, e.g., monobutyl tin dihydroxychloride $(C_4H_9)Sn(OH)_2Cl$. The reactants and catalyst are heated at a temperature of about 150° C. to about 200° C., preferably from about 180° C. to about 190° C., for five to six hours. Then excess 2-ethylhexanol is removed under vacuum and a mixture of silica gel, aluminum oxide, magnesium oxide and potassium oxide is added. The product is then obtained by filtration.

An alternative photostabilizing chromophore of formula (1) can be made by first treating, for example, ethyl α-cyano-β,β-diphenylacrylate with 2,2-dimethyl-1,3-propanediol (neopentyl glycol). Here, a five-fold excess of neopentyl glycol is combined with the ethyl α-cyano-β,β-diphenylacrylate and a catalytic amount of sodium carbonate. The mixture is heated and ethanol generated by the reaction is removed by distillation. When the reaction is completed, toluene is added and the sodium carbonate is filtered off while the solution is still hot. The product solution is washed several times with water and then the solution is concentrated to afford crystallization of a product. This product can then be treated with undecanoic acid (alternatively a polyester), and methanesulphonic acid in toluene; heated and any water formed during the reaction is distilled from the mixture. This product mixture is then washed twice with a solution of NaCl in water. The product is then filtered and dried. The final photostabilizing chromophore made by the above procedure is greater than 99% pure and does not require further purification. The overall reaction described above is summarized as follows:

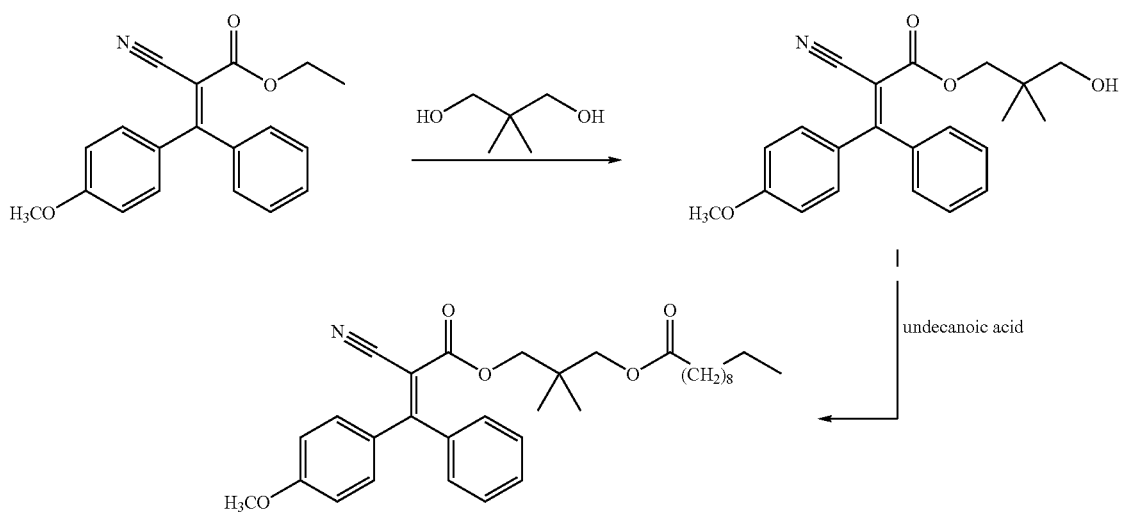

An additional photostabilizing chromophore of formula (1) can be made by first treating, for example, octanol with one or more equivalents of caprolactone. This alcohol-ester is reacted with ethyl α-cyano-β,β-diphenylacrylate to yield a photostabilizing chromophore, by the methods outlined above.

Still another photostabilizing chromophore of formula (1) can be made by first treating a naphthalate polyester with a diol, e.g. ethylene glycol. The resulting naphthalate-alcohol can then be treated with ethyl α-cyano-β,β-diphenylacrylate to yield a photostabilizing chromophore. The overall reaction described above is summarized as follows:

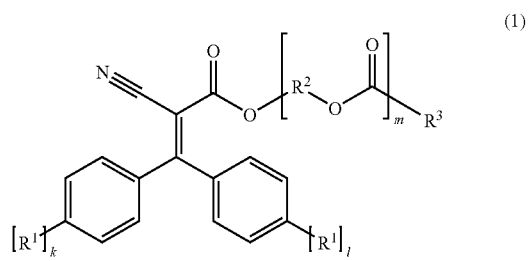

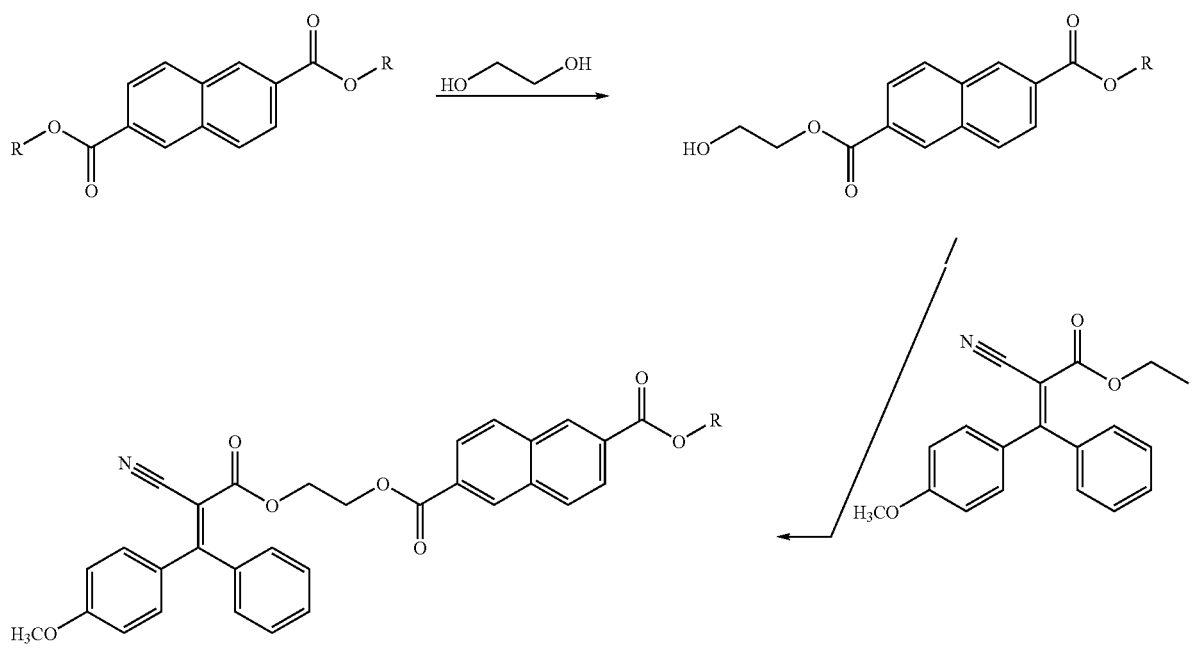

The use of the variable R in the above reaction scheme should be understood to be any applicable chemical group and is commonly familiar to one of ordinary skill in the art as a variable that does not prohibit the disclosed reaction. Alternatively, the ethyl α-cyano-β,β-diphenylacrylate is first treated with an excess of a diol, e.g. ethylene glycol. The resulting α-cyano-β,β-diphenylacrylate alcohol is then treated with a naphthalate polyester to yield the analogous product. Generally, one of ordinary skill can perform the disclosed synthetic methodologies to yield the photostabilizing chromophores of the present invention.

The foregoing description is given for clearness of understanding only, and no unnecessary limitations should be understood therefrom, as modifications within the scope of the invention may be apparent to those having ordinary skill in the art.

What is claimed is:

1. A method of quenching fluorescence and excited state energy of a naphthalate compound that is subjected to UV-radiation in an amount sufficient to cause the naphthalate compound to reach an excited state and fluoresce, comprising adding to the naphthalate compound, in a sunscreen composition, a fluorescence quenching amount of a compound of formula (1):

wherein $R^1$ is an alkoxy; $R^2$ is an organic linker; $R^3$ is selected from a group consisting of a straight or branched $C_1$-$C_{30}$ alkyl, a straight or branched $C_1$-$C_{30}$ alkenyl, a straight or branched $C_1$-$C_{30}$ alkynyl, and a polymer; k is either zero or one; l is either zero or one, wherein the sum of k+l is one; and m is an integer in a range from zero to about twenty.

2. The method of claim 1, wherein m is an integer in a range from one to about twenty, and the organic linker is selected from a group consisting of $CH_2$, $CH_2CH_2$, $CH_2CH_2CH_2$, $CH_2CH(CH_3)CH_2$, $CH_2C(CH_3)_2CH_2$, $CH_2OCH_2$, $CH_2CH_2OCH_2CH_2$, and mixtures thereof.

3. The method of claim 2, wherein m is equal to one and the organic linker is $CH_2C(CH_3)_2CH_2$.

4. The method of claim 1, wherein the alkoxy ($R^1$) has 1 to about 5 carbon atoms.

5. The method of claim 4, wherein the alkoxy ($R^1$) is selected from a group consisting of methoxy and ethoxy.

6. The method of claim 5, wherein the alkoxy ($R^1$) is methoxy.

7. The method of claim 5, wherein the alkoxy ($R^1$) is ethoxy.

8. The method of claim 1, wherein $R^3$ is a branched C3-C30 alkyl.

9. The method of claim 8, wherein $R^3$ is ethylhexyl.

10. The method of claim 1, wherein the alkoxy ($R^1$) is methoxy, $R^3$ is ethylhexyl, and m is equal to zero.

11. The method of claim 1, wherein the naphthalate compound is selected from a group consisting of naphthalate polymer; naphthalate copolymer; naphthalate oligomer; dialkylnaphthalate; mixtures and blends thereof.

12. The method of claim 11, wherein the naphthalate compound is a polyethylene napthalate polymer.

13. The method of claim 12, wherein the naphthalate compound is poly(ethylene 2,6-naphthalenedicarboxylate).

14. The method of claim 11, wherein the naphthalate compound is ethylhexyl naphthalate.

* * * * *